United States Patent
Rogers et al.

(10) Patent No.: US 10,815,475 B2
(45) Date of Patent: *Oct. 27, 2020

(54) METHOD AND COMPOSITION

(71) Applicant: ARCIS BIOTECHNOLOGY HOLDINGS LIMITED, Warrington (GB)

(72) Inventors: Jan Rogers, Chester (GB); Carlos Toro Rueda, Madrid (ES)

(73) Assignee: ARCIS BIOTECHNOLOGY HOLDINGS LIMITED, Warrington (GB)

( * ) Notice: Subject to any disclaimer, the term of this patent is extended or adjusted under 35 U.S.C. 154(b) by 251 days.

This patent is subject to a terminal disclaimer.

(21) Appl. No.: 15/748,929

(22) PCT Filed: Jul. 28, 2016

(86) PCT No.: PCT/GB2016/052317
§ 371 (c)(1),
(2) Date: Jan. 30, 2018

(87) PCT Pub. No.: WO2017/017458
PCT Pub. Date: Feb. 2, 2017

(65) Prior Publication Data
US 2019/0002870 A1    Jan. 3, 2019

(30) Foreign Application Priority Data
Jul. 30, 2015  (GB) .................................. 1513492.7

(51) Int. Cl.
*C12Q 1/68* (2018.01)
*C12N 15/10* (2006.01)
*C12Q 1/686* (2018.01)
*C12Q 1/6806* (2018.01)
*C12Q 1/6851* (2018.01)

(52) U.S. Cl.
CPC ......... *C12N 15/1003* (2013.01); *C12Q 1/686* (2013.01); *C12Q 1/6806* (2013.01); *C12Q 1/6851* (2013.01); *C12Q 2521/107* (2013.01); *C12Q 2527/125* (2013.01); *C12Q 2531/113* (2013.01)

(58) Field of Classification Search
CPC ......................... C12N 15/1003; C12Q 1/6806
USPC ....................................................... 435/6.12
See application file for complete search history.

(56) References Cited

U.S. PATENT DOCUMENTS 10,364,427 B2 * 7/2019 Cobb ................. C12N 15/1003

FOREIGN PATENT DOCUMENTS

| CN | 101886142 A | 11/2010 | |
|---|---|---|---|
| JP | 2005192554 A | 7/2005 | |
| WO | 2011163249 A2 | 12/2011 | |
| WO | 2013121222 A1 | 8/2013 | |
| WO | 2013175188 A1 | 11/2013 | |
| WO | WO-2013175188 A1 * | 11/2013 | ........... C12Q 1/6806 |
| WO | 2014155078 A1 | 10/2014 | |
| WO | 2016051177 A2 | 4/2016 | |

OTHER PUBLICATIONS

Isquith et al., "Surface-Bonded Antimicrobial Activity of an Organosilicon Quaternary Ammonium Chloride", Applied Microbiology, vol. 24, No. 6, Dec. 1972, pp. 859-863.
Repetto et al., "An improved DNA isolation technique for PCR detection of Strongyloides stercoralis in stool samples", Acta Tropica 126 (2013) pp. 110-114.
International Search Report & Written Opinion for PCT Application No. PCT/GB2016/052317 dated Sep. 14, 2016, 11 pages.

* cited by examiner

*Primary Examiner* — Jezia Riley
(74) *Attorney, Agent, or Firm* — Hoffman Warnick LLC

(57) ABSTRACT

A method of extracting DNA and/or RNA from a cell or capsid, the method comprising steps of: (a) contacting a composition comprising the cell or capsid with a composition comprising (ii) a quaternary ammonium compound or a precursor thereof; and (b) contacting the composition obtained in step (a) with a composition comprising a proteinaceous washing agent.

2 Claims, No Drawings

METHOD AND COMPOSITION

The present invention relates to methods and compositions for use in DNA and/or RNA extraction.

Methods of DNA extraction are well known in the art and have several applications across diagnostics, pharmaceuticals, and research. For example, such methods are used in the genetic engineering of plants and animals, for the diagnosis of many medical conditions, in the manufacture of a number of pharmaceuticals, and in genetic fingerprinting and crime scene investigations. In most of these methods it is necessary to amplify the extracted DNA or RNA, and typically extracted DNA or RNA must be purified prior to use in an amplification process.

Prior art processes for obtaining DNA and/or RNA for use in amplification methods involve several steps, including a purification step. These may necessitate the use of magnetic beads, silica beads or centrifugation.

In many applications the isolated purified DNA or RNA is used in a PCR (polymerase chain reaction) method. PCR methods are very well known to the person skilled in the art. For many PCR techniques a sample having a high degree of purity is essential to achieve reliable results. This is also the case for cloning and sequencing and other amplification techniques such as isothermal amplification.

Problems with current methods of DNA and/or RNA extraction include the complexity of the multi-step process, the amount of time taken to complete the process, the cost of the reagents and instruments required, and the potentially low yields of DNA or RNA as material may be lost during the purification steps.

It is an aim of the present invention to provide a method of extracting DNA and/or RNA from a cell or capsid which overcomes at least one of the disadvantages of the prior art.

The present invention seeks in particular to provide a method of obtaining DNA and/or RNA that can be directly used in an amplification process, for example a method of obtaining DNA and/or RNA that can be used directly in PCR, sequencing or cloning methods. The DNA and/or RNA could also be used amplification processes such as isothermal amplification, loop-mediated isothermal amplification (LAMP), strand displacement amplification (SDA), helicase-dependant amplification (HDA) and nicking enzyme amplification reaction (NEAR).

It would also be desirable to provide DNA and/or RNA that can be used in chip-on-chip applications and hybridisation probes.

According to a first aspect of the present invention there is provided a method of extracting DNA and/or RNA from a cell or capsid, the method comprising steps of:
  (a) contacting a composition comprising the cell or capsid with a composition comprising
    (i) a quaternary ammonium compound or a precursor thereof; and
  (b) contacting the composition obtained in step (a) with a composition comprising a proteinaceous washing agent.

The method of the present invention may involve extraction of DNA. The method may involve the extraction of RNA. The method of the present invention may involve extraction of DNA and RNA.

The DNA and/or RNA may be extracted from any suitable cell or capsid. Capsids are the protein shells of viruses that enclose the genetic material. The virus may be any suitable virus.

The cells may be selected from prokaryotic, eukaryotic or archaeal cells. The cells may be obtained from Gram-positive or Gram-negative bacteria, mycobacteria, mycoplasma, fungi, or parasitic organisms; or from animals or plants. The cells may be animal cells, for example cells derived from humans, mammals or other animals. The cells may be plant cells. The cells may be a human or animal tissue cell. The cells may be selected from connective, muscle, nervous or epithelial tissue cells. The cells may be obtained from a bodily fluid of a human or animal, for example blood, mucus, sputum, urine, vomit or other excrement.

Exemplary Gram-negative bacteria include, but are not limited to, bacteria of the genera *Bacteroides, Bartonella, Bordetella, Borrelia, Brucella, Campylobacter, Chlamydia, Escherichia, Francisella, Haemophilus, Helicobacter, Klebsiella, Legionella, Leptospira, Moraxella, Neisseria, Pasteurella, Proteus, Pseudomonas, Salmonella, Shigella, Spirillum, Streptobacillus, Treponema, Vibro*, and *Yersinia*. Exemplary Gram-positive bacteria include, but are not limited to, bacteria of the genera *Actinomyces, Bacillus, Clostridium, Corynebacterium, Listeria, Nocardia, Peptostreptococcus, Propionibacterium, Staphylococcus, Streptococcus*, and *Streptomyces*.

Exemplary fungal cells include any species of *Aspergillus* Exemplary yeast cells include, but are not limited to, any species of *Pichia, Saccharomyces, Schizosaccharomyces*, or *Schwanniomyces*

Parasitic cells include, but are not limited to, those belonging to the genera *Acanthamoeba, Ancylostoma, Ascaradia, Babesia, Balamuthia, Balantidium, Brugia, Clonorchis, Cryptosporidium, Dicrocoelium, Dicytocaulus, Dientamoeba, Diphylobothrium, Dirofilaria, Echinococcus, Echinostoma, Entamoeba, Enterobius, Fasciola, Fascioloides, Giardia, Hymenolepsis, Isospora, Leishmania, Mesocestoides, Moniezia, Necator, Naegleria, Onchocerca, Opisthorchis, Paragonimus, Plasmodium, Rhabditida, Schistosoma, Spirurida, Strongyloides, Taenia, Trichomonas, Trichuris, Toxocara, Trypanosoma, Uncinaria* and *Wuchereria*.

The cells may be connective tissue cells. Connective tissue cells include storage cells such as brown or white adipose cells and liver lipocytes, extracellular matrix (ECM)-secreting cells such as fibroblasts, chondrocytes, and osteoblasts, and blood/immune system cells such as lymphocytes (T lymphocytes, B lymphocytes, or plasma cells), granulocytes such as basophils, eosinophils, and neutrophils, and monocytes. The cells may be an epithelial cell. Epithelial cell types include gland cells specialized for secretion such as exocrine and endocrine glandular epithelial, and surface epithelial cells such as keratinizing and non-keratinizing surface epithelial cells. The cells may be a nervous tissue cell. Nervous tissue cells include glia cells and neurons of the central or peripheral nervous system. The cells may be muscle cells. Muscle tissue cells include skeletal, cardiac, and smooth muscle cells. Many of these cell types can be further divided. The cells may be of endodermal, mesodermal, or ectodermal origin. The cells may be stem cells or mature, differentiated cells. Exemplary stem cells include hematopoietic stem cells, neural stem cells, and mesenchymal stem cells. Exemplary mature, differentiated cell types include adipocytes such as white fat cells or brown fat cells, cardiac myocytes, chondrocytes, endothelial cells, exocrine gland cells, fibroblasts, hepatocytes, keratinocytes, macrophages, monocytes, melanocytes, neurons, neutrophils, osteoblasts, osteoclasts, pancreatic islet cells such as beta cells, skeletal myocytes, smooth muscle cells, B cells, plasma cells, T lymphocytes such as regulatory, cytotoxic, and helper, and dendritic cells.

Viruses may be a DNA virus or an RNA virus. Viruses include, but are not limited to, those of the families Adenoviridae, Arenaviradae, Arteriviridae, Ascoviridae, Asfarviridae, Astroviridae, Baculoviridae, Barnaviridae, Birnaviridae, Bornaviridae, Bromoviridae, Bunyaviridae, Caliciviridae, Caulimoviridae, Comoviridae, Coronaviridae, Chrysoviridae, Circoviridae, Closteroviridae, Cystoviridae, Dicistroviridae, Entomopoxvirinae, Filoviridae, Flaviviridae, Flexiviridae, Geminiviridae, Guttaviridae, Hepadnaviridae, Hepeviridae, Herpesviridae, Hypoviridae, Iflaviridae, Inoviridae, Iridoviridae, Leviviridae, Luteoviridae, Marnaviridae, Microviridae, Mimiviridae, Myoviridae, Nanoviridae, Narnaviridae, Nidovirales, Nimaviridae, Orthomyxoviridae, Papovaviridae, Papillomaviridae, Parvoviridae, Paramyxoviridae, Picornaviridae, Podoviridae, Polyomaviridae, Potyviridae, Poxyiridae, Pseudoviridae, Reoviridae, Retroviridae, Rhabdoviridae, Roniviridae, Rudiviridae, Sequiviridae, Siphoviridae, Tetraviridae, Togaviridae, Tombusviridae, Totiviridae and Tymoviridae. Exemplary viruses include, but are not limited to, Adenovirus, Cowpox virus, Dengue virus, Ebola virus, Epstein-Barr virus, Enterobacteria phage T4, Foot-and-mouth disease virus, Hepatitis A virus, Hepatitis B virus, Hepatitis C virus, Herpes simplex virus type 1, Herpes simplex virus type 2, Human adenovirus C, Human b-lymphotrophic virus, Human immunodeficiency virus, Human Poliovirus, Human T-cell lymphotrophic virus, Infectious hematopoietic necrosis virus, Infectious pancreatic necrosis virus, Influenza viruses types A, B, and C, ME virus, Measles virus (rubeola virus), Mengovirus, Mumps virus, Myxoma virus, Papilloma virus, Parainfluenza virus, Poliovirus, Rabies virus, Rhinovirus, Rotavirus, Rubella virus, and Yellow fever virus.

The cells or capsids may be indicative of disease. In some embodiments the cells may be cancer cells. Examples include, but are not limited to, cancers derived from brain cells, epithelial cells (carcinoma), connective tissue (sarcoma), hematopoietic cells (lymphoma and leukemia), pluripotent cells (germ cell tumour), and embryonic tissue (blastoma). In another embodiment the cells may be indicative of an autoimmune disease. Autoimmune diseases commonly affect organ and tissue types such as blood vessels, connective tissues, endocrine glands, joints, muscles, red blood cells, and the skin. Examples of autoimmune disorders include, but are not limited to, Addison's disease, celiac disease, dermatomyositis, Graves' disease, Guillan-Barre disease, inflammatory bowel disease, multiple sclerosis, pernicious anaemia, psoriasis, rheumatoid arthritis, systemic lupus erythematosus and type 1 diabetes. In a further embodiment the cells may be indicative of a disease that may be caused by a pathogen. The pathogen may be viral, bacterial, fungal, parasitic, or prionic.

In some embodiments the composition comprising the cell or capsid may be a sample extracted from a plant or animal. For example the cell or capsid may be present in a sample of bodily fluid obtained from a human or animal. Suitable bodily fluids include blood and blood components, mucus, saliva, urine, vomit, faeces, sweat, semen, vaginal secretion, tears, pus, sputum and pleural fluid.

It is particularly advantageous that bodily fluid samples can be used directly in the method of the present invention. For example it is possible to carry out the method of the present invention on cells or capsids present in a whole blood sample or a sputum sample.

In preferred embodiments the method of the present invention involves extracting DNA and/or RNA from a cell or capsid present in a blood sample, preferably a whole blood sample.

Preferably the composition comprising the cell or capsid is a blood sample, preferably a whole blood sample.

Step (a) of the method of the present invention involves contacting the composition comprising the cell or capsid with a composition comprising (i) a quaternary ammonium compound or a precursor thereof.

Any suitable quaternary ammonium compound may be included in component (i).

Some suitable quaternary ammonium compounds have the structure (I):

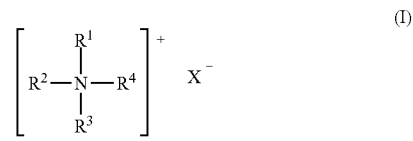

wherein each of $R^1$, $R^2$, $R^3$ and $R^4$ is an optionally substituted alkyl, alkenyl, alkylaryl or aryl group and $X^-$ is a suitable anion. Preferably each of $R^1$, $R^2$, $R^3$ and $R^4$ is an optionally substituted alkyl or alkylaryl group, more preferably an unsubstituted alkyl or alkylaryl group.

Any suitable anion $X^-$ may be used. $X^-$ may be selected from halide, acetate, nitrite, a lower alkyl sulfate, carbonate or alkyl carboxylate. Preferably $X^-$ is chloride or bromide.

Each of $R^1$, $R^2$, $R^3$ and $R^4$ may be an unsubstituted alkyl group having from 1 to 30 carbon atoms or an alkylaryl group, for example a benzyl group.

Preferably at least one of $R^1$, $R^2$, $R^3$ and $R^4$ is an unsubstituted alkyl group having at least 6 carbon atoms, preferably at least 8 carbon atoms.

In one preferred embodiment $R^1$ is an alkyl group having from 6 to 30 carbon atoms, preferably from 8 to 24 carbon atoms, suitably from 8 to 20 carbon atoms, for example from 10 to 18 carbon atoms and most preferably from 12 to 16 carbon atoms; each of $R^2$ and $R^3$ is an alkyl group having from 1 to 4 carbon atoms, preferably methyl and $R^4$ is an alkyl group having from 1 to 4 carbon atoms, preferably methyl or an alkylaryl group, preferably benzyl. The skilled person will appreciate that such compounds may often be present as a mixture of homologues.

Suitable quaternary ammonium compounds of this type include benzyldialkyl methyl ammonium chloride and dialkyl dimethyl ammonium chloride in which the alkyl groups have 10 to 24 carbon atoms.

Some preferred quaternary ammonium compounds of this type include didecyl dimethyl ammonium chloride and dimethyl benzyl alkyl ammonium chloride in which the alkyl group contains a mixture of $C_8$ to $C_{16}$ alkyl chains.

Some suitable quaternary ammonium compounds include a substituted pyridinium compound for example an alkyl or alkenyl substituted pyridinium compound. Examples include pyridinium compounds having an alkyl or alkenyl substituent of 8 to 30, preferably 10 to 20 carbon atoms. Preferred counterions are halides. One suitable compound of this type is cetylpyridinium chloride.

Some suitable precursor compounds of this type are compounds including a guanidine moiety. The composition may comprise a compound which does not contain a permanent cation but which is protonated in solution at the pH at which the composition is used. These may be referred to as precursors to quaternary ammonium compounds. Preferred are non-polymeric guanidine compounds. Examples of such compounds include chlorhexidine salts, Chlorhexidine gluconate is especially preferred.

In some especially preferred embodiments of the method of the first aspect of the present invention the composition comprising the cell or capsid is contacted with a composition comprising a quaternary ammonium compound including a silicon-containing functional group. By silicon-containing group we mean to refer to any group including a silicon atom. Preferred silicon-containing functional groups are those which include a silicon atom covalently bonded via four single bonds to four organic moieties. The silicon atom may be directly bonded to oxygen and/or carbon atoms.

Preferably the method of the first aspect of the present invention component (i) comprises a compound of general formula (II):

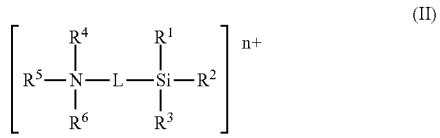

or a derivative salt thereof wherein L is a linking group; each of $R_1$, $R^2$, $R^3$, $R^4$, $R^5$ and $R^6$ is independently selected from H or an optionally substituted alkyl, alkenyl, aryl or alkoxy group; and n is 0 or 1.

It will be appreciated that in embodiments in which n is 1, the species shown in formula (I) is a cationic species.

In such embodiments the species of formula (I) will be present as an adduct or salt including a suitable counterion. However for ease of reference, in this document we may make general reference to compounds of formula (I) and any such reference includes where appropriate any counterion which must be present.

Any suitable counterion may be used. Monovalent counterions are preferred. Suitable counterions include halides and oxyhalo ions for example chloride, bromide, bromite, chlorite, hypochlorite, chlorate, bromate and iodate. In a most preferred embodiment the counterion is a chloride ion.

In this specification any optionally substituted alkyl, alkenyl, aryl or alkoxy group may be optionally substituted with one or more substituents selected from halo, hydroxy, nitro, mercapto, amino, alkyl, alkoxy, aryl, sulfo and sulfoxy.

Preferred substituents which may be present in the alkyl, alkenyl, aryl or alkoxy groups defined herein are halogens, in particular fluorine. In particular each of $R^1$, $R^2$, $R^3$, $R^4$, $R^5$ or $R^6$ may comprise fluoroalkyl or fluoroalkoxy groups which may comprise one or more fluorine atoms.

Each of $R^1$, $R^2$ and $R^3$ is independently selected from an optionally substituted alkyl, alkenyl, aryl or alkoxy group. Preferably at least one of $R^1$, $R^2$ and $R^3$ is an optionally substituted alkoxy group. More preferably each of $R^1$, $R^2$ and $R^3$ is an optionally substituted alkoxy group, most preferably each is an unsubstituted alkoxy group. The alkyl group of the alkoxy group may be straight chained or branched. Preferably each of $R^1$, $R^2$ and $R^3$ is an alkoxy group having from 1 to 20 carbon atoms, preferably from 1 to 16 carbon atoms, more preferably from 1 to 12 carbon atoms, preferably from 1 to 8 carbon atoms, suitably from 1 to 6 carbon atoms, more preferably from 1 to 4 carbon atoms.

In preferred embodiments each of $R^1$, $R^2$ and $R^3$ is independently selected from methoxy, ethoxy, propoxy, butoxy and isomers thereof. Most preferably each of $R^1$, $R^2$ and $R^3$ is selected from methoxy, ethoxy and isopropoxy. Preferably each of $R^1$, $R^2$ and $R^3$ is selected from methoxy and ethoxy. Most preferably each of $R^1$, $R^2$ and $R^3$ is methoxy. Preferably each of $R^1$, $R^2$ and $R^3$ is the same.

$R^4$ and $R^6$ is preferably an alkyl group having from 1 to 8 carbon atoms, most preferably 1 to 6 carbon atoms, more preferably 1 to 4 carbon atoms. $R^4$ and $R^6$ may suitably be selected from methyl, ethyl, propyl, butyl and isomers thereof. Preferably $R^4$ and $R^6$ is methyl or ethyl. Most preferably $R^4$ and $R^6$ is methyl.

Preferably $R^5$ is an alkyl group having from 8 to 30 carbon atoms, for example from 10 to 26 carbon atoms, suitably from 12 to 24 carbon atoms, preferably from 14 to 22 carbon atoms, suitably from 16 to 20 carbon atoms, for example 17 to 19 carbon atoms, suitably 18 carbon atoms.

L is a linking group. It may suitably be a bond or an optionally substituted alkylene, alkenylene or arylene group. Preferably L is an optionally substituted alkenylene group. It may be substituted along the chain or within the chain. For example L may be an ether linking moiety, i.e. a group of formula $O(CH_2)_n$ in which n is 1 to 12, preferably 1 to 6.

Preferably L is an unsubstituted alkylene group, more preferably an alkylene group having 1 to 12 carbon atoms, preferably 1 to 10 carbon atoms, suitably 1 to 8 carbon atoms, for example 2 to 8 carbon atoms, more preferably 2 to 6 carbon atoms, suitably 2 to 5 carbon atoms for example 2 to 4 carbon atoms. In especially preferred embodiments L is a propylene group.

In especially preferred embodiments of the compound of formula (I), $R^1$, $R^2$ and $R^3$ are each $C_1$ to $C_4$ alkoxy, L is a $C_2$ to $C_5$ alkylene group, $R^4$ and $R^6$ are each $C_1$ to $C_4$ alkyl groups and $R^5$ is a $C_{12}$ to $C_{24}$ alkyl group.

Most preferably the compound of formula (I) is the compound shown in formula (IV). This compound is commercially available as a solution in methanol.

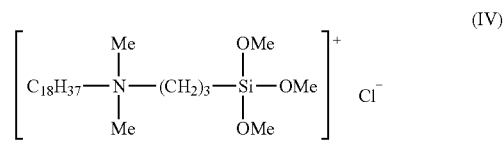

The skilled person will appreciate that commercial sources of such compounds may include some residual starting material and other minor impurities.

Preferably component (i) is selected from quaternary ammonium salts of formula (I), pyridinium salts, guanidine salts and compounds of formula (II).

Most preferably component (i) comprises a compound of formula (IV).

In preferred embodiments the composition contacted with the cell or capsid in step (a) of the method of the present invention further comprises (ii) a non-ionic surfactant.

Component (ii) may be selected from any suitable non-ionic surfactant. Suitable non-ionic surfactants will be known to the person skilled in the art and include alcohol ethoxylates, fatty acid esters and alkyl polyglycosides.

Non-ionic surfactants may have a hydrophilic portion, suitably an alkoxylate moiety or a sugar moiety. Suitable non-ionic surfactants include alcohol ethoxylates and fatty alcohol polyglycosides. Suitably the hydrophilic-lipophilic balance (HLB) value of a non-ionic surfactant used in the present invention is at least 7, and preferably at least 10. Especially suitable non-ionic surfactants may have an HLB value falling in the range 10-16, preferably 10-14. For the purposes of these definitions HLB value is determined by the classical method of Griffin (Griffin W C: "Calculation of HLB Values of Non-Ionic Surfactants," Journal of the Society of Cosmetic Chemists 5 (1954): 249).

Preferred non-ionic surfactants for use herein include hydrocarbyl saccharide compounds. By hydrocarbyl-saccharide compound we mean to refer to a compound including a hydrocarbyl group and a saccharide moiety.

The hydrocarbyl group may be bound to the saccharide moiety via a carbon-carbon bond or via a carbon-oxygen bond. Preferably it is bound to the saccharide moiety via a carbon-oxygen bond, for example via an ester linkage or an ether linkage. Most preferably it is bound to the oligosaccharide moiety via an ether linkage. Thus in preferred embodiments the non-ionic surfactant is a hydrocarbyl ether of a saccharide moiety.

The hydrocarbyl-saccharide compound may include one or more hydrocarbyl groups. Preferably it comprises one hydrocarbyl group. The hydrocarbyl group may be an optionally substituted alkyl, alkenyl or alkynylene group. Most preferably it is an optionally substituted alkyl group. Suitable substituents include halo, hydroxy, nitro, mercapto, amino, alkyl, alkoxy, aryl, sulfo and sulfoxy. Any substitution may be within the chain or along it, for example the chain may include an ether linkage.

Preferably the hydrocarbyl group is an unsubstituted alkyl group. It may be straight chained or may be branched. Most preferably it is straight chained. Especially preferred hydrocarbyl groups are alkyl groups having from 1 to 30 carbon atoms, preferably 2 to 24 carbon atoms, more preferably from 4 to 20 carbon atoms, suitably from 4 to 16 carbon atoms, preferably from 6 to 14 carbon atoms, for example from 6 to 12 carbon atoms and most preferably from 8 to 10 carbon atoms. Preferred are straight chained alkyl groups having from 6 to 12 carbon atoms.

The saccharide moiety of the hydrocarbyl oligosaccharide species may include from 1 to 10 monosaccharide species. Thus it may be a monosaccharide unit, a disaccharide unit or an oligosaccharide unit. Preferably the saccharide moiety comprises from 2 to 8, suitably from 2 to 6, preferably from 2 to 5, for example 3 or 4 monosaccharide units. Any suitable monosaccharide unit may be included. Preferred saccharides include allose, altrose, glucose, mannose, gulose, idose, galactose and talose.

Mixtures of two or more monosaccharides may be present in the saccharide moiety. Preferably the saccharide moiety comprises glucose. More preferably all of the monosaccharide units present in the saccharide moiety are glucose.

In a preferred embodiment the non-ionic surfactant is an alkyl polyglucoside (APG), preferably a monoalkyl-polyglucoside. Suitably the non-ionic surfactant is a compound of general formula (III):

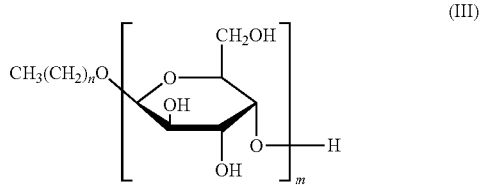

(III)

wherein n is from 5 to 12, preferably from 6 to 10, more preferably from 7 to 9 and m is from 1 to 6, preferably from 2 to 5, more preferably 3 or 4.

The composition contacted with the composition comprising the cell or capsid in step (a) of the method of the first aspect may be provided in any suitable form. It may consist essentially of component (i) or component (i) and a solvent. It may consist essentially of components (i) and (ii) or it may comprise one or more further components. Suitably the composition includes one or more solvents. Preferred solvents are water and water miscible solvents. In embodiments in which the quaternary ammonium compound is obtained commercially as a solution in methanol, much of the methanol is suitably removed prior to use of the compound in the method of the present invention.

Preferably the composition is aqueous. In especially preferred embodiments water comprises at least 90 wt %, more preferably at least 95 wt % or at least 99 wt % of cell solvents present in the composition. In one preferred embodiment the composition is freeze dried. In such embodiments an aqueous mixture may be provided upon contact with an aqueous composition comprising the cells or capsids. Freeze-dried compositions may be advantageous for storage and distribution.

In some embodiments the composition used in step (a) may be immobilised on a solid support, for example on a resin bead or on a planar substrate.

The composition used in step (a) of the method of the present invention may include a mixture of two or more quaternary ammonium compounds and/or a mixture of two or more non-ionic surfactants.

The composition contacted with the cell or capsid in step (a) of the method of the present invention preferably comprises at least 0.0001 wt % of a quaternary ammonium compound, preferably at least 0.0005 wt %, more preferably at least 0.001 wt %, and more preferably at least 0.002 wt %.

The quaternary ammonium compound preferably comprises up to 10 wt % of the composition contacted with the cell or capsid in step (a), suitably up to 5 wt %, preferably up to 1 wt %, preferably up to 0.1 wt %, more preferably up to 0.01 wt %, and more preferably up to 0.005 wt %.

In embodiments in which more than one quaternary ammonium compound is present, the above amounts refer to the total of all such compounds.

Suitable non-ionic surfactants include any compound that improves the solubility, especially the solubility in water, of the quaternary ammonium compound including a silicon-containing functional group.

The non-ionic surfactant is suitably present in the composition contacted with the cell or capsid in step (a) in an amount of at least 0.0001 wt %, preferably at least 0.0005 wt %, more preferably at least 0.001 wt %, and more preferably at least 0.002 wt %.

The non-ionic surfactant may be present in the composition contacted with the cell or capsid in step (a) in an amount of up to 10 wt % of the composition, suitably up to 5 wt %, preferably up to 1 wt %, preferably up to 0.1 wt %, more preferably up to 0.01 wt %, and more preferably up to 0.005 wt %.

In embodiments in which the composition comprises two or more non-ionic surfactants the above amounts refer to the total of all such compounds.

The weight ratio of the quaternary ammonium compound functional component to the non-ionic surfactant is preferably from 1:10 to 10:1, preferably from 1:5 to 5:1, preferably from 1:3 to 3:1, suitably from 1:2.5 to 2.5:1.

The composition contacted with the composition comprising the cell or capsid in step (a) preferably has a pH of from 6 to 8.

The composition contacted with the cell or capsid preferably comprises (i) a quaternary ammonium compound and (ii) a non-ionic surfactant. In some embodiments the composition may consist essentially of these components.

In some embodiments the composition further includes a solvent, preferably water.

Other components may also be present, for example magnesium chloride and tris buffers. However this is not preferred.

Suitably components (i) and (ii), which may each comprise a mixture of components, together make up at least 50 wt % of all ingredients other than solvent present in the composition used in step (a), preferably at least 70 wt %, more preferably at least 90 wt %, preferably at least 95 wt %, for example at least 99 wt %.

Preferably the composition used in step (a) of the method of the present invention comprises less than 0.01 mmol of magnesium ions, preferably less than 0.001 mmol.

In step (a) of the method of the first aspect of the present invention the composition comprising the cell or capsid is contacted with a composition comprising (i) a quaternary ammonium compound and optionally (ii) a non-ionic surfactant. Suitably the ratio of the sample composition (i.e. the composition comprising the cell or capsid) to the composition used in step (a) is from 10:1 to 1:1000, preferably from 5:1 to 1:100, suitably from 1:1 to 1:20 for example from 1:3 to 1:10, by volume.

Suitably the composition is agitated to ensure mixing and then incubated at room temperature for a period of from 1 second to 24 hours, suitably from 5 seconds to 1 hour, preferably from 5 seconds to 30 minutes, preferably from 10 seconds to 15 minutes, suitably from 20 seconds to 10 minutes, preferably from 30 seconds to 5 minutes, for example for about 40 to 100 seconds, suitably for about 1 minute. Although shorter incubation times are preferred the composition is stable for 24 hours.

This material is suitably used directly in step (b) of the method of the present invention.

Step (b) of the method of the first aspect of the present invention involves contacting the composition obtained in step (a) with a composition comprising a proteinaceaous washing agent. Suitably there are no purification steps between step (a) and step (b) and the material obtained in step (a) is used directly in step (b). Step (b) involves contacting a composition obtained in step (a) with a composition containing an proteinaceous washing agent.

Preferred proteinaceous washing agents are anionic proteins.

Suitable proteinaceous washing agents include tryptone, gelatin, casein and bovine serum albumin (BSA). Preferred proteinaceous washing agents include bovine serum albumin and casein. An especially preferred washing agent is BSA. Acetylated bovine serum albumin (BSA) is particularly preferred.

Suitably the proteinaceous washing agent is present in the composition used in step (b) in an amount from 0.01 to 50 wt %, preferably 0.1 to 10 wt %, suitably from 0.1 to 5 wt %, for example about 1 wt %.

Suitably the composition used in step (b) of the method of the first aspect of the present invention is an aqueous composition. Suitably water comprises at least 90 wt % of all solvents present in the composition, preferably at least 95 wt % for example at least 99 wt % of all solvents present in the composition.

In one embodiment the composition may be freeze dried. In such an embodiment an aqueous mixture may be provided upon contact with the aqueous composition obtained in step (a).

In step (b) of the method of the present invention suitably the composition obtained in step (a) is added to a composition containing the proteinaceous washing agent in a ratio of from 10:1 to 1:100, preferably from 5:1 to 1:50, suitably from 1:1 to 1:10.

It should be noted that the method of the present invention does not necessarily include using all of the mixture obtained in step (a) in step (b). In many instances a portion of the composition obtained in step (a) is contacted with the composition comprising the proteinaceous washing agent in step (b).

Suitably in step (b) of the method of the present invention the mixture is briefly agitated at room temperature. It may be left for a period of 1 second to 24 hours, suitably 5 seconds to 1 hour, preferably 5 seconds to 30 minutes, preferably 10 seconds to 10 minutes, suitably from 30 seconds to 5 minutes, for example about 1 minute.

It has been surprisingly found that the mixture obtained in step (b) of the present invention can be used directly in a DNA or RNA amplification method.

It is highly advantageous that the method of the present invention provides a simple process in which DNA or RNA suitable for amplification can be obtained directly from whole blood.

Suitable DNA amplification methods will be known to the person skilled in the art. Preferred DNA amplification methods include sequencing, cloning and PCR.

According to a second aspect of the present invention there is provided a kit comprising:
(a) a first composition comprising
    (i) a quaternary ammonium; and optionally
    (ii) a non-ionic surfactant; and
(b) a second composition comprising an proteinaceous washing agent.

Preferred features of the composition of the second aspect are as defined in relation to the first aspect.

In some embodiments the composition of the first aspect may be a bead or solid substrate which carries the reagents.

An advantage of the method of the first aspect of the present invention is that the extracted DNA and/or RNA can be used in subsequent applications without the need for isolation or purification steps.

According to a third aspect of the present invention there is provided a method of identifying a component of genetic material, the method comprising the steps of:
(a) contacting a composition comprising a cell or capsid with a composition comprising:
    (i) a quaternary ammonium compound; and optionally
    (ii) a non-ionic surfactant;
(b) contacting the composition obtained in step (a) with a composition comprising an proteinaceous washing agent; and
(c) using the material obtained in step (b) in an amplification method.

Steps (a) and (b) are suitably as defined in relation to the first aspect.

The preferred features of the third aspect are defined in the relation to the first and second aspects of the present invention.

Suitably there are no purification steps between step (b) and step (c).

Suitably step (c) is carried out on the material directly obtained in step (b).

Step (c) involves amplifying the DNA or RNA obtained in steps (a) and (b).

The amplification method may be a sequencing method, a cloning method or it may involve a method of identifying the DNA and/or RNA. Such methods will be known to the person skilled in the art.

In some embodiments step (c) may involve using recombinart DNA technology.

Step (c) may involve a purification method.

Step (c) may include a chip-on-chip method.

In some embodiments in step (c) of the method of the third aspect the extracted DNA and/or RNA obtained in step (b) is used as a template in a polymerase chain reaction (PCR).

PCR step (b) can be carried out by any means known to those skilled in the art. Suitable PCR techniques include basic PCR, reverse transcription (RT)-PCR, hot-start PCR, long PCR, quantitative endpoint PCR, quantitative real-time PCR, rapid amplified polymorphic DNA analysis, nested PCR and high-fidelity PCR.

In step (c) of the method of the third aspect of the present invention the extracted DNA and/or RNA may used as a template in PCR. As will be appreciated by the skilled person PCR techniques may be used for a number of purposes. The method of the third aspect may comprise a method of identifying a component of genetic material. In step (b) some or all of the DNA and/or RNA extracted in step (a) may be identified. Step (b) may involve confirming that a small portion of DNA and/or DNA matches a known sample. Step (b) may involve a DNA cloning step; genetic finger printing, for example in forensic applications; functional analysis of genes; diagnosis of heredity disease; and detection or diagnosis of infectious disease.

In some embodiments the method of the third aspect of the present invention may be used in the detection or diagnosis of a disease. The method may be used to detect or diagnose, among others, genetic diseases, cancers, autoimmune diseases and pathogenic infections. Genetic markers indicative of the disease are identified in a PCR step (c). A particular advantage of the present invention is that because samples containing cells or capsids do not need to be purified before or after steps (a) or (b), there is a significant reduction in the time taken to reach a diagnosis.

Because the present invention can be carried out on impure samples it enables the method of the third aspect to be carried out quickly and easily and at low cost. This has significant advantages for example in the detection of diseases in less developed countries where expensive laboratory facilities are not routinely available. It is envisaged that the method of the present invention could be carried out to detect a disease on whole blood or sputum samples at mobile clinics.

A further advantage of the compositions used in the present invention is that they are highly effective at releasing DNA and/or RNA from a wide variety of cells and capsids. The present invention may provide a method by which the genetic material in a sample can be retained but in a form which is no longer active. This is potentially very useful when dealing with samples containing infectious pathogens.

In some embodiments step (c) involves a method of cloning the DNA and/or RNA extracted in steps (a) or (b).

In some embodiments step (c) involves a method of sequencing the DNA and/or RNA obtained in steps (a) and (b).

In some embodiments the present invention may provide a method of decontaminating a biological sample containing a cell or capsid.

Such a method may be applicable to any suitable sample containing cells or capsids. In one exemplary embodiment, a blood sample taken from a patient suffering from malaria can be made safe by the method of the first aspect as the *Plasmodium* parasite is destroyed in the process. In another exemplary embodiment a blood sample taken from a patient suffering from human immunodeficiency virus would no longer pose a risk to downstream users if it had been treated according to the method of the first aspect since the capsid of the virus would be destroyed.

This is advantageous because samples treated according to such a method may be transferred by regular post.

The methods and compositions of the present invention may have applications in pharmaceuticals, diagnostics, medical research, biological research, chemical research, and forensics.

The present invention will now be further described with reference to the following non-limiting examples.

EXAMPLE 1

Compositions were prepared comprising 0.003 wt % of an alkyl polyglucoside of formula (III) as described herein and 0.003 wt % of a quaternary ammonium compound.

The following quaternary ammonium compounds were used:

| Composition | Quaternary ammonium compound |
|---|---|
| A | The compound of formula (IV) |
| B | Chlorohexadine digluconate |
| C | Cetylpyridinium chloride |
| D | Benzyl dimethyl alkyl ammonium chloride |

As previously described the compound of formula (IV) has the structure:

$$\left[ C_{18}H_{37} - \underset{\underset{Me}{|}}{\overset{\overset{Me}{|}}{N}} - (CH_2)_3 - \underset{\underset{OMe}{|}}{\overset{\overset{OMe}{|}}{Si}} - OMe \right]^+ Cl^-$$

The alkyl group of the benzyl dimethyl alkyl ammonium chloride contains a mixture of $C_8$ to $C_{16}$ alkyl chains.

30 μl of a blood sample was mixed with 170 μl of each of compositions A, B, C and D and shaken briefly. The compositions were then incubated for 1 minute at room temperature.

2.5 μl of the resultant mixture was then mixed with 10 μl of a composition comprising 1 wt % BSA. This mixture was then used directly in PCR.

A PCR for hRNaseP was performed with hRnaseP-ARCIS kit.

Each extracted sample was loaded in duplicate.

Reaction mixture for ARCIS extraction

TaqMan Master Mix: 12.5 μl
Primer forward: 0.5 μl
Primer reverse: 0.5 μl
1 uM RnaseP Probe: 0.5 μl
H₂O: 6 μl
DNA: 5 μl I of extracted solution

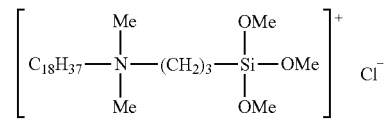
Mixture volume: 20 μm

PCR Conditions

| | |
|---|---|
| Mix activation | 50° C. 2 min |
| Initial denaturation | 95° C. 10 min |
| Denaturation | 95° C. 15 sec |
| Annealing | 60° C. 60 sec |

Denaturation and Annealing: 45 cycles

Results (Ct Values)

| Composition A | Composition B | Composition C | Composition D |
|---|---|---|---|
| 27.53 | 27.77 | 27.44 | 27.47 |
| 27.61 | 27.79 | 27.24 | 27.48 |

EXAMPLE 2

The procedure of example 1 was repeated for composition A but 20 µl of a composition comprising 1 wt % casein was used instead of the composition comprising BSA. This gave PCR results of 32.04 and 33.6.

The invention claimed is:

1. A method of identifying a component of genetic material, the method comprising the steps of:
   (a) contacting a composition comprising a cell or capsid with a composition comprising:
      (i) a quaternary ammonium compound; and optionally
      (ii) a non-ionic surfactant;
   (b) contacting the composition obtained in step (a) with a composition comprising a proteinaceous washing agent; and
   (c) using the material obtained in step (b) in an amplification method.

2. A method according to claim 1 wherein there are no purification steps between step (b) and step (c).

* * * * *